United States Patent [19]

Swartz et al.

[11] Patent Number: 5,656,028
[45] Date of Patent: *Aug. 12, 1997

[54] PROCESS FOR THE NONSURGICAL MAPPING AND/OR TREATMENT OF ECTOPIC ATRIAL TACHYCARDIA USING A GUIDING INTRODUCER

[75] Inventors: John F. Swartz, Tulsa, Okla.; John D. Ockuly, Minnetonka; James A. Hassett, Bloomington, both of Minn.

[73] Assignee: Daig Corporation, Minnetonka, Minn.

[*] Notice: The term of this patent shall not extend beyond the expiration date of Pat. No. 5,575,766.

[21] Appl. No.: 434,051

[22] Filed: May 2, 1995

Related U.S. Application Data

[63] Continuation-in-part of Ser. No. 272,014, Jul. 8, 1994, which is a continuation-in-part of Ser. No. 147,168, Nov. 3, 1993, Pat. No. 5,497,774, and Ser. No. 146,744, Nov. 3, 1993, Pat. No. 5,427,119.

[51] Int. Cl.$^6$ ............................................ A61M 37/00
[52] U.S. Cl. ................... 604/53; 609/21; 609/22; 609/281; 128/772; 607/122
[58] Field of Search ....................... 604/280, 281, 604/22, 53, 21; 600/16–18; 128/772, 642, 695, 702, 705; 607/122, 96, 101, 115, 119

[56] References Cited

U.S. PATENT DOCUMENTS

| | | |
|---|---|---|
| 4,033,331 | 7/1977 | Guss et al. . |
| 4,117,836 | 10/1978 | Erikson . |
| 4,641,649 | 2/1987 | Walinsky et al. . |
| 4,882,777 | 11/1989 | Narula . |
| 4,883,058 | 11/1989 | Ruiz . |
| 4,898,591 | 2/1990 | Jang et al. . |
| 4,945,912 | 8/1990 | Langberg . |
| 4,976,691 | 12/1990 | Sahota ............................ 604/280 X |
| 5,016,640 | 5/1991 | Ruiz . |
| 5,203,776 | 4/1993 | Durfee ............................ 604/280 X |
| 5,215,540 | 6/1993 | Anderhub . |
| 5,231,994 | 8/1993 | Harmjanz . |
| 5,242,441 | 9/1993 | Avitall . |
| 5,269,326 | 12/1993 | Verrier . |
| 5,295,484 | 3/1994 | Marcus et al. ............... 607/115 X |
| 5,299,574 | 4/1994 | Bower . |
| 5,327,905 | 7/1994 | Avitall ............................ 128/772 |
| 5,423,882 | 6/1995 | Jackman et al. ............... 607/122 |
| 5,427,119 | 6/1995 | Swartz et al. ............... 128/772 |
| 5,488,960 | 2/1996 | Toner ............................ 128/772 |

OTHER PUBLICATIONS

Walsh, Edward P. "Ablation of Ectopic Atrial Tachycardia in Children" Radiofrequency Catheter Ablation of Cardiac Arrhythmias, Chap. 23 (1994).
Singer, I. et al. "Catheter Ablation for Arrhythmias" Clinical Manual of Electrophysiology, p. 421–431 (1993).
Falk, R.H. et al "Atrial Fibrillation Mechanisms and Management," pp. 359–374 (1992).
Gallagher, J.J. et al. "Catheter Technique for Closed Chest Ablation of the Atrioventricular Conduction System" N. Engl. J. Med, vol. 306, pp. 194–200 (1982).
Tracy, C.M. "Radiofrequency Catheter Ablation of Ectopic Atrial Tachycardia Using Paced Activation Sequence Mapping" J. Am. Coll. Cardiol., vol. 21, pp. 901–917, (1993).
Saul, J.P. et al. "Catheter Ablation of Accessory Atrioventricular Pathways in Young Patients: Use of Long Vascular Sheaths, the Transseptal Approach and a Retrograde Left Posterior Parallel Approach" J. Amer. Coll. Card., vol. 21, No. 3, pp. 571–583 (1993).
Swartz, J.F. et al. "Radiofrequency Endocardial Catheter Ablation of Accessory Atrioventricular Pathway Atrial Insertion Sites", Circulation, vol. 87, No. 2, pp. 487–499 (1993).

*Primary Examiner*—V. Millin
*Assistant Examiner*—Chalin Smith
*Attorney, Agent, or Firm*—Scott R. Cox

[57] ABSTRACT

A process for the treatment of ectopic atrial tachycardia by use of ablation and/or mapping procedures comprising ablating discrete locations within the right atrium of the heart by use of an ablation catheter and a precurved guiding introducer. Also disclosed is a shape for the guiding introducer to be used for the ablation and/or mapping of the discrete locations within the right atrium for the treatment of ectopic atrial tachycardia.

13 Claims, 2 Drawing Sheets

PROCESS FOR THE NONSURGICAL MAPPING AND/OR TREATMENT OF ECTOPIC ATRIAL TACHYCARDIA USING A GUIDING INTRODUCER

CROSS REFERENCE TO RELATED APPLICATIONS

This application is a continuation-in-part of application Ser. No. 08/272,014, filed Jul. 8, 1994 which is a continuation-in-part of Ser. No. 08/147,168, Nov. 3, 1993, Pat. No. 5,497,774 and also a continuation-in-part of Ser. No. 08/146,744, Nov. 3, 1993, U.S. Pat. No. 5,427,119.

BACKGROUND OF THE INVENTION

1. Field of Invention

This invention relates to a process for the mapping and treatment of atrial arrhythmia using catheters guided by a shaped guiding introducer. In addition, it relates to a preferred shape of the guiding introducer which is used with a mapping or ablation catheter for the mapping or treatment of ectopic atrial tachycardia.

2. Prior Art

Introducers and catheters have been in use for medical procedures for many years. For example, one use is to convey an electrical stimulus to a selected location within the human body. Another use is to assist in the monitoring and measuring for diagnostic tests within the human body. Thus, catheters may assist in examination, diagnosis and treatment within a human body while positioned at a specific location, which is otherwise inaccessible without more invasive procedures. In use, catheters may be inserted into a vein or artery which is near the body surface. These catheters are then guided to a specific location for examination, diagnosis or treatment by manipulating the catheter through the artery or vein of the human body.

Catheters have become increasingly useful in remote and difficult to reach locations within the body. However, the utilization of these catheters is frequently limited because of the need for a precise placement of the electrodes of the catheter at a specific location within the body.

Control of the movement of catheters to achieve such precise placement is difficult because of the inherent structure of the catheter. The body of a conventional catheter is long and tubular. To provide sufficient control of the movement of the catheter, it is necessary that its structure be somewhat rigid. However, the catheter must not be so rigid as to prevent the bending or curving necessary for movement through the vein, artery or other body part to arrive at the specified location. Further, the catheter must not be so rigid as to cause damage to the artery or vein while it is being moved within the body.

While it is important that the catheter not be so rigid as to cause injury, it is also important that there be sufficient rigidity in the catheter to accommodate torque control, i.e., the ability to transmit a twisting force along the length of the catheter. Sufficient torque control enables controlled maneuverability of the catheter by the application of a twisting force at the proximal end of the catheter that is transmitted along the catheter to its distal end. The need for greater torque control often conflicts with the need for reduced rigidity to prevent injury to the body vessel.

Catheters are used increasingly for medical procedures involving the human heart. In these procedures a catheter is typically advanced to the heart through veins or arteries and then is positioned at a specified location within the heart. Typically, the catheter is inserted in an artery or vein in the leg, neck, upper chest or arm of the patient and threaded, often with the aid of a guidewire or introducer, and guided through various arteries or veins until the tip of the catheter reaches the desired location in the heart.

The distal end of a catheter used in such a procedure is sometimes preformed into a desired curvature so that by torquing the catheter about its longitudinal axis, the catheter can be guided to the desired location within the heart or in the arteries or veins associated with the heart. For example, U.S. Pat. No. 4,882,777 discloses a catheter with a complex curvature at its distal end for use in a specific procedure in the right ventricle of a human heart. U.S. Pat. Nos. 5,299,574 and 4,117,836 disclose a catheter for the selective coronary angiography of the left coronary artery and U.S. Pat. Nos. 5,295,574, 5,215,540, 5,016,640 and 4,883,058 disclose catheters for selective coronary angiography of the right coronary artery. See also U.S. Pat. No. 4,033,331. U.S. Pat. No. 5,269,326 discloses a method for transvenously accessing the pericardial space through the right atrium for particular medical procedures. U.S. Pat. No. 4,898,591 discloses a catheter with inner and outer layers containing braided portions. The '591 patent also discloses a number of different curvatures for intravascular catheters. See also U. S. Pat. Nos. 5,231,994, 4,838,879, 5,171,232 and 5,290,229.

Atrial fibrillation is the most common sustained heart arrhythmia. It is estimated to occur in upwards of 0.4 percent of the adult population and perhaps as many as 10 percent of the population who are 60 years or older. Cox, J. L., et al., *Electrophysiology, Pacing and Arrhythmia*, "Operations for Atrial Fibrillation," Clin. Cardiol. 14, 827–834 (1991). Atrial arrhythmia may be transient or persistent. While most atrial arrhythmia occurs in individuals having other forms of underlying heart disease, some atrial arrhythmias occur independently. While atrial arrhythmias do not directly cause death as frequently as ventricular arrhythmias, they increase the risk factor for a number of other diseases such as strokes, thrombosis, atherosclerosis, systemic and cerebral embolism and cause a number of additional medical problems.

Certain patients with symptomatic or life threatening atrial arrhythmias, however, cannot be adequately treated by drugs or common medical devices, such as defibrillation, or by cardioversion. Other forms of treatment are then mandated, which may include surgery.

Another procedure used for treatment of certain types of cardiac arrhythmia within the last 10 to 15 years is catheter ablation. This procedure has been used to interrupt or modify existing conduction pathways associated with ventricular arrhythmias within the heart. The particular area for ablation depends on the type of underlying arrhythmia. One common ablation procedure is for the treatment of atrioventricular (AV) nodal reentrant tachycardia. With this problem ablation of the fast or slow AV nodal pathways has become an accepted treatment. See Singer, I., et al., "Catheter Ablation for Arrhythmias" *Clinical Manual of Electrophysiology*, pp. 421–431 (1993). The use of ablation catheters for ablating locations within the heart has been disclosed, for example in U.S. Pat. Nos. 4,641,649, 5,263, 493, 5,231,995, 5,228,442 and 5,281,217. However, none utilize a guiding introducer to guide an ablation catheter to a particular location in the heart.

In addition, catheter ablation for the treatment of ectopic atrial tachycardia is disclosed, for example, in Walsh, Edward P. "Ablation of Ectopic Atrial Tachycardia in Children" *Radio Frequency Catheter Ablation of Cardiac*

*Arrhythmias*, Chap. 23 (1994). See also Tracey, C. N. "Radio Frequency Catheter Ablation of Ectopic Atrial Tachycardia Using Paced Activation Sequence Mapping" J. Am. Coll. Cardial. Vol 21, pp. 910–917 (1993).

The sources of energy used for catheter ablation vary. Initially, high voltage, direct current (D.C.) ablation techniques were commonly used. However, because of problems associated with the use of D.C. current, radio frequency (R.F.) ablation has become a preferred source of energy for the ablation procedures. The use of RF energy for ablation has been disclosed, for example, in U.S. Pat. Nos. 4,945,912, 5,209,229, 5,281,218, 5,242,441, 5,246,438, 5,281,213 and 5,293,868. Other energy sources being considered for ablation of heart tissue include laser, ultrasound, microwave and fulgutronization.

Ablation of a precise location within the heart requires the precise placement of the ablation catheter within the heart. Precisely positioning of the ablation catheter is especially difficult because of the physiology of the heart, particularly as the ablation procedures generally occur while the heart is beating. Commonly, the placement of the catheter is determined by a combination of electrophysiological guidance and fluoroscopy (placement of the catheter in relation to known features of the heart which are marked by radiopaque diagnostic catheters which are placed in or at known anatomical structures such as the coronary sinus, high right atrium and the right ventricle).

While these techniques have been useful for certain arrhythmias, catheter ablation is still a difficult, time consuming procedure.

Accordingly, it is an object of this invention to disclose a process for the mapping and treatment of ectopic atrial tachycardia in the right atrium by the use of an ablation catheter guided to a specific location by a shaped, guiding introducer.

It is a still further object of the invention to disclose a particular shape for a guiding introducer for use with a catheter for mapping and ablation of ectopic atrial arrhythmia within the right atrium.

It is a further object of this invention to prepare a shaped guiding introducer for use in electrophysiology procedures for the treatment of ectopic atrial tachycardia.

These and other objects can be obtained by the disclosed process for the treatment of ectopic atrial tachycardia and the design of the shaped, guiding introducer for use with that process which are disclosed by the instant invention.

SUMMARY OF INVENTION

The instant invention is a process for the treatment and/or mapping of ectopic atrial tachycardia by the use of mapping and ablation catheters comprising:

introducing into the right atrium a mapping or ablation catheter placed within a shaped, guiding introducer and mapping or ablating a selected site within the right atria.

The instant invention also discloses a specifically designed shape for a guiding introducer for use with mapping and/or ablation catheters in the mapping and/or treatment of ectopic atrial tachycardia in the right atrium.

DETAILED DESCRIPTION OF THE PREFERRED EMBODIMENT

Figure 1:
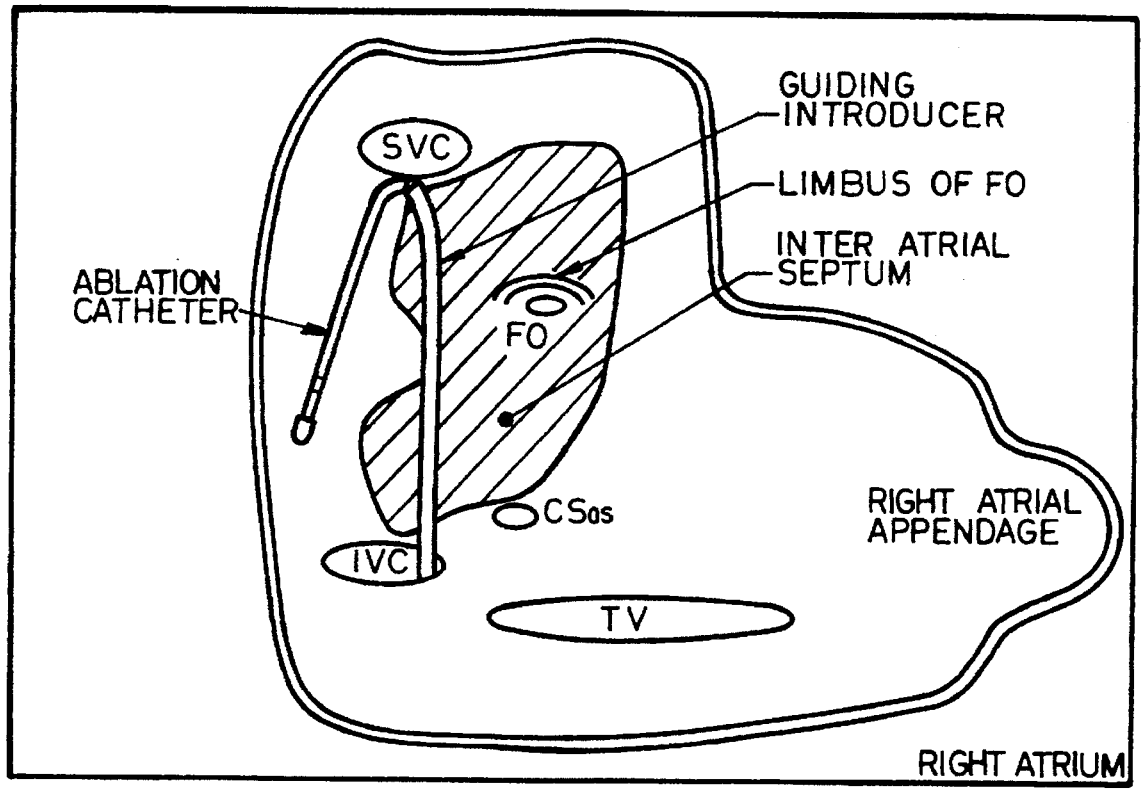
FIG. 1 is a schematic drawing of the right atrium showing the use of a guiding introducer for the right atrium as shown in FIGS. 2A, 2B and 2C for the treatment of ectopic atrial tachycardia.

A typical human heart includes a right ventricle, a right atrium, left ventricle and left atrium. The right atrium is in fluid communication with the superior vena cava and the inferior vena cava. The atrioventricular septum separates the right atrium from the right ventricle. The tricuspid valve contained within the atrioventricular septum communicates the right atrium with the right ventricle. On the inner wall of the right atrium where it is connected with the left atrium is a thin walled, recessed portion, the fossa ovalis. A detailed schematic drawing of the right atrium is shown in FIG. 1. Between the fossa ovalis and the tricuspid valve is the opening or ostium for the coronary sinus. The coronary sinus is the large epicardial vein which accommodates most of the venous blood which drains from the myocardium into the right atrium.

In the normal heart, contraction and relaxation of the heart muscle (myocardium) takes place in an organized fashion as electro-chemical signals pass sequentially through the myocardium from the sinoatrial (SA) node to the atrialventricular (AV) node and then along a well defined route which includes the His-Purkinje system into the left and right ventricles. Initial electric impulses are generated at the SA node and conducted to the AV node. The AV node lies near the ostium of the coronary sinus in the interatrial septum in the right atrium. The His-Purkinje system begins at the AV node and follows along the membranous interatrial septum toward the tricuspid valve through the atrioventricular septum and into the membranous interventricular septum. At about the middle of the interventricular septum, the His-Purkinje system splits into right and left branches which straddle the summit of the muscular part of the interventricular septum.

Sometimes abnormal rhythms occur in the atrium which are referred to as atrial arrhythmia. Three of the most common arrhythmia are ectopic atrial tachycardia, atrial fibrillation and atrial flutter.

Atrial fibrillation can result in significant patient discomfort and even death because of a number of associated problems, including: (1) an irregular heart rate which causes the patient discomfort and anxiety, (2) loss of synchronous atrioventricular contractions which compromises cardiac hemodynamics resulting in varying levels of congestive heart failure, and (3) stasis of blood flow, which increases the vulnerability to thromboembolism. It is sometimes difficult to isolate a specific pathological cause for the atrial fibrillation although it is believed that the principle mechanism is one or a multitude of reentry circuits within the left and/or right atrium. Efforts to alleviate these problems in the past have included significant usage of pharmacological treatments.

Another type of atrial arrhythmia is ectopic atrial arrhythmia ("EAT"). EAT is an uncommon rhythm disorder that involves rapid impulse generation from a single atrial focus outside the sinuatrial node. In many circumstances EAT may occur for long periods of time, possibly leading to cardiomyopathy. Because EAT is one of the few reversible causes of cardiomyopathy, more effective treatment of EAT is sought. Radio frequency ablation for the treatment of EAT is disclosed in Walsh, Edward P., "Ablation of Ectopic Atrial Tachycardia in Children," *Radio Frequency Catheter Ablation of Cardia Arrhythmias*, Chap. 23 (1994). See also Tracey, C. N. "Radio Frequency Catheter Ablation of Ectopic Atrial Tachycardia Using Paced Activation Sequence Mapping" J. Am. Coll. Cardiol. Vol 21, pp. 210–917 (1993).

While pharmacological treatments are sometimes effective, in some circumstances drug therapy is ineffective and frequently is plagued with side effects such as dizziness, nausea, vision problems and other difficulties.

In the last few years surgical procedures have also been utilized in the treatment of atrial arrhythmia. The goal of these surgical procedures parallel that of the pharmacological treatments, to relieve both the subjective symptoms of atrial arrhythmia as well as to normalize hemodynamics by restoring regular atrial contributions to the cardiac output.

The ablation catheters used to perform the ablation procedures produce scar tissue at the selected site or location within the atria. The energy necessary to scar or ablate the tissue can be provided from a number of different sources. Originally direct current was utilized to provide the energy for ablation procedures. More recently the preferred choice of energy source has been radio frequency energy (R.F.). Laser, microwave, ultrasound, low and high energy direct current and fulgutronization procedures have also been utilized to perform ablation procedures. The preferred source of energy for the ablation procedures of the instant invention is R.F. energy.

One of the significant difficulties in performing any cardiac procedure in the atria is caused by the physiology of the atria themselves when beating, especially if that beating is abnormal. The preferred procedure for the treatment of EAT within the right atrium thus requires the precise positioning and contact pressure of the ablation catheter within the right atrium to ablate a predetermined location within the right atrium.

Mere introduction of an ablation catheter into the right atrium without precise placement and precise contact pressure will not be sufficient to satisfactorily ablate the desired location. This precise placement and contact pressure cannot be produced without the use of a specialized precurved, guiding introducer to guide the ablation catheter to the correct location and to permit adequate pressure to be placed on the ablation catheter to produce an adequately ablated location.

An element in the treatment of EAT also includes sensing of the location of EAT in the right atrium to efficiently and accurately map the atria. The physiology of the heart and its beating also interferes with the effectiveness of mapping catheters. The guiding introducer of the instant invention can also assist in the precise placement of such a mapping catheter.

Medical practitioners often monitor the introduction of cardiac catheters and their progress through the vascular system by use of fluoroscopes. Unfortunately, fluoroscopes can not easily identify specific features in the heart, in general, and the critically important structures of the right atrium in specific, thus making placement and utilization of an ablation catheter extremely difficult without a curved, guiding introducer. This placement is especially difficult as the beating heart is in motion, resulting in the catheter moving within the atria as blood is being pumped through the heart. The structure and shape of the guiding introducer of the instant invention addresses and solves these problems and permits the precise placement necessary for accurate ablation procedures. In addition, because of this difficulty in placement, excessive fluoroscopy frequently occurs, which is undesirable.

The shaped, guiding introducer of the instant application positions the mapping and/or ablation catheter at the precise location necessary for the procedure as a result of its unique shape. The specially designed guiding introducer is produced from conventional elongated catheters. Although this guiding introducer is described as having multiple sections, preferably, they are produced during a conventional introducer production procedure and formed as a single unitary structure. Additional features of the guiding introducers other than its unique shape include radiopaque tip markers and vents, which will be discussed in more detail later.

Although in the preferred embodiment a single guiding introducer is used to assist the ablation catheter in ablating a particular location within the right atrium, alternatively a pair or more guiding introducers may be used in combination to create the appropriate shaped guiding introducer. For example, a first shaped guiding introducer may be placed within a second shaped guiding introducer wherein the combination of the shape of the first and second guiding introducers operating together will create the desired shape depending upon the rotation of the first and second guiding introducer and the extent of the extension of the inner guiding introducer within the outer guiding introducer.

Where a single guiding introducer is used for this procedure, the guiding introducer is used to guide the catheter to a specific location in the right atrium. With the precurved, guiding introducer holding the ablation catheter in a predetermined location, the ablation catheter then ablates the predetermined location. More than one ablation procedure may be necessary to fully ablate the location of the EAT. Sensing elements within the catheter also can be used to sense activity around that location.

Figure 2C:
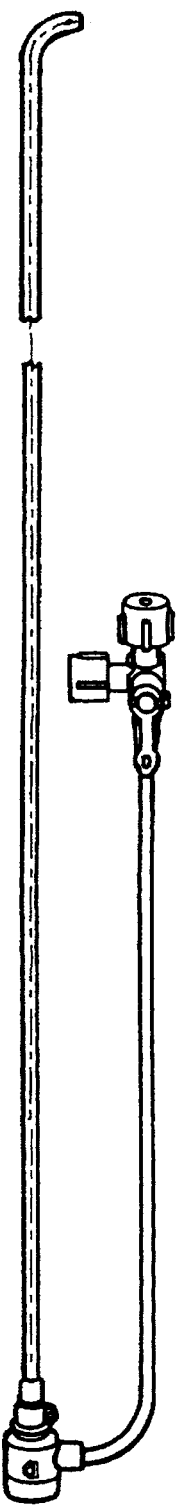
FIG. 2C is a third view of the guiding introducer of FIG. 2A rotated 180° from the position of FIG. 2A such that the side port tubing is directly to the right of the guiding introducer but generally in the same plane thereof.
Figure 2B:
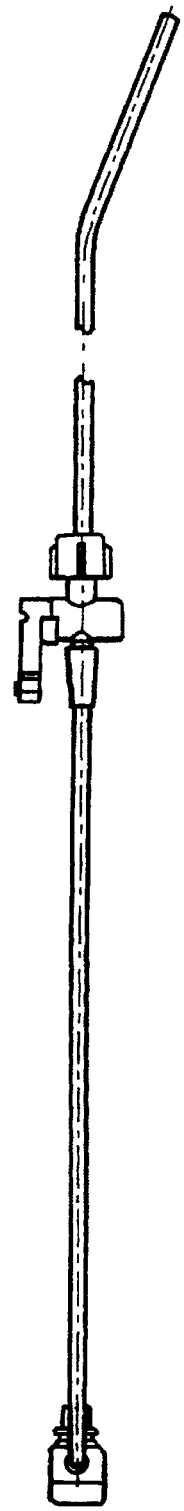
FIG. 2B is a second view of the guiding introducer of FIG. 2A wherein the guiding introducer is rotated 90° clockwise from the position of FIG. 2A such that the side port tubing is positioned on top of a portion of the first section of the third guiding introducer.
Figure 2A:
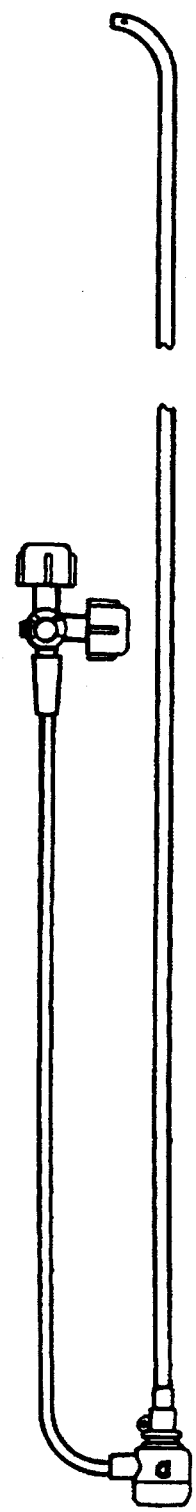
FIG. 2A is a first view of the guiding introducer of the instant invention for use in the right atrium as shown in FIG. 1 with the side port tubing, which is attached to the proximal end of the guiding introducer, directly to the left of the guiding introducer but generally in the same plane thereof.

One common location for EAT in the right atrium is along the crista terminalis around and between the superior and inferior vena cava. See FIG. 1. The guiding introducer used to guide an ablation and/or mapping catheter to the desired location in the right atrium associated with the crista terminalis has a preferred shape. This guiding introducer is divided into three sections as shown in FIGS. 2A, 2B and 2C. (The guiding introducer is shown in three different views. In each of the views the guiding introducer will be secured to a valve for attachment to a conventional tubing and stop cock. In each such arrangement, the shape of the guiding introducer will be described making reference to its position in relation to the side port tubing where the proximal end of the guiding introducer is secured in place. In the first of these three figures, the side port is generally in the plane of the first straight section of the guiding introducer but directed 90° to the left (see FIG. 2A). In the second drawing, the side port is rotated 90° clockwise such that the stop cock and the remaining portion of the tubing appear to cover a portion of the first section of the guiding introducer. See FIG. 2B. The third drawing (FIG. 2C) rotates the side port tubing 90° further clockwise, such that it is once again generally in the same plane as the first section of the guiding introducer but with the side port tubing on the right side of the drawing.)

The first section of the guiding introducer for treatment of EAT in the right atrium is a conventional, generally elongated hollow, straight introducer section of sufficient length for introduction into the patient and for manipulation from the point of insertion to the specific desired location within the right atrium of the heart. Merged with the distal end of the first section of the guiding introducer is a second section which is comprised of a curved portion, curving to the right as shown in FIG. 2B. The inner angle of this curve is from about 180° to about 130° and preferably from about 170° to about 150°. The radius of the curved portion is from about 1.20 to 2.20 in. and preferably from about 1.50 to about 2.00 in. At the end of this curved portion begins the third section which is first a generally straight portion of about 0.50 to 2.00 in. and preferably from about 1.00 to about 1.60 in. in length, concluding in a curved portion to the right as shown in FIG. 2C (or to the left in FIG. 2A) at an inner angle of about 50° to about 130° and preferably from about 70° to about 110°. The radius of this curved portion is from about 0.10 to about 0.70 in. and preferably from about 0.30 to about 0.50 in. At the end of this curved portion is the distal tip of the guiding introducer. Preferably the overall length of this curved portion of the third section, beginning at the proximal end of the curved portion and extending to the distal tip, is from about 0.20 to about 1.00 in. and more preferably from about 0.40 to about 0.70 in. The distal tip of this guiding introducer may and preferably will be tapered to form a good transition with a dilator.

The shape of the sections of the guiding introducer may be modified by use of one or more straight or curved sections as long as the overall shape of the guiding introducer is approximately as described above.

The distal tip of the guiding introducer may be, and preferably will be, tapered to form a good transition with a dilator. This tapering is preferably less than 10° and more preferably about 4° to about 7°. The guiding introducer preferably may also contain one or a multitude of radiopaque tip marker bands near the distal tip of the introducer. This guiding introducer also preferably contains one or a plurality of vents near the distal tip of the guiding introducer, preferably three or four such vents. The vents are preferably located no more than about 1.00 in. from the tip of the guiding introducer and more preferably 0.10 to about 1.00 in. from the tip. The size of these vents should be in the range of about 40 to about 60/1000 of an inch in diameter. These vents are generally designed to prevent air from entering the guiding introducer caused by the withdrawal of the catheter contained within the guiding introducer in the event the distal end of the guiding introducer is occluded. For example, if the tip of the guiding introducer is placed against the myocardium and the catheter located within the guiding introducer is withdrawn, a vacuum may be created within the guiding introducer if no vents are provided. If such vacuum is formed, air may be forced back into the guiding introducer by the reintroduction of the catheter into the lumen of the guiding introducer. Such air could cause significant problems in the patient, including those associated with air embolisms such as the possibility of a stroke, heart attack or other such problems. The addition of vents near the distal tip of the guiding introducer prevents the formation of such vacuum by permitting fluid, presumably blood, to be drawn into the lumen of the guiding introducer as the catheter is being removed from the guiding introducer, thus preventing the possibility of formation of air within the guiding introducer.

The guiding introducer may be made of any material suitable for use in humans which has a memory or permits distortion from, and substantial return to, the desired three dimensional or complex multiplanar shape. For the purpose of illustration and not limitation, the internal diameter of the guiding introducer may vary from about 6 to about 12 "French" (1 French equals ⅓ of a millimeter). Such guiding introducer can accept dilators from about 6 to about 12 French and appropriate guidewires. Obviously, if larger or smaller dilators or catheters are used in conjunction with the guiding introducer of the instant invention, modifications in size or shape can be made to the instant guiding introducer.

Variations in size and shape of the guiding introducer are also intended to encompass pediatric uses for the guiding introducer of the instant invention, although the preferred uses are for adult human hearts. It is well recognized that pediatric uses may require reductions in size of the various sections of the guiding introducer, in particular the first section, but without any significant modification to the shape or curve of the guiding introducer.

In addition, variations in size or shape of the guiding introducer are also intended to encompass the specialized situations that sometimes occur in patients with enlarged and rotated hearts.

In operation, a modified Seldinger technique is normally used for the insertion of the guiding introducer and ablation catheter into the body. Using this procedure, a small skin incision is made at the appropriate location to facilitate the catheter or dilator passage. Subcutaneous tissue is then dissected, followed by a puncture of the vessel with an appropriate needle with stylet positioned at a relatively shallow angle. The needle is then partially withdrawn and reinserted at a slightly different angle into the vessel making sure that the needle remains within the vessel. The soft flexible tip of an appropriate size guidewire is then inserted through, and a short distance beyond, the needle into the vessel. Firmly holding the guidewire in place, the needle is removed. The guidewire is then advanced through the vessel into the right femoral vein and through the inferior vena cava into the right atrium. (The preferred procedure uses the inferior approach to the right atrium. Procedures for the superior approach to the right atrium can also be used. However, the shape of the guiding introducer must be modified to adjust for this alternative approach.) With the guidewire in place, the dilator is then placed over the guidewire with the guiding introducer placed over the dilator. The dilator and the guiding introducer generally form an assembly to be advanced together along the guidewire into the inferior vena cava. After insertion of the assembly, the guidewire is then withdrawn.

The guiding introducer for use in the right atrium is then passed over the guidewire to perform ablation and/or mapping procedures in the right atrium to treat and eliminate EAT. Several separate ablation procedures at the specific location may be necessary to achieve complete ablation. Sensing catheters can be used in the right atrium to assure that complete ablation has been accomplished. Once it has been determined that complete ablation has occurred, the guiding introducer is removed.

By use of the guiding introducer in coordination with fluoroscopic viewing, the distal portion of the appropriate catheter can be manipulated to the correct location within the right atrium. In addition, by providing sufficient rigidity and support, as the guiding introducer is held in place by the various anatomical structures of the heart, as well as the vascular surfaces, the distal end of the guiding introducer can be maintained at that fixed location or surface position of the endocardial structure to permit the appropriate ablation. The precise location of the ablation catheter is important as there will be no dilution of the energy delivered due to the unfocused energy being dissipated over the entire cardiac chamber and lost in the circulating blood by a constantly moving tip of the ablating catheter. This permits a significantly reduced amount of energy to be applied during the ablation procedure. Further, time used to perform the procedure is significantly reduced over procedures where no guiding introducer is used. In addition, by this ablation procedure the same types of destruction of the discrete location can be achieved as have been accomplished, for example, in previous surgical procedures.

It will be apparent from the foregoing that while particular forms of the invention have been illustrated and described, various modifications can be made without departing from the spirit and scope of the invention. Accordingly, it is not intended that this invention be limited except as by the appended claims.

We claim:

1. A procedure for the treatment of ectopic atrial tachycardia within the right atrium of a human heart comprising introducing into the right atrium a precurved, guiding introducer, wherein said introducer contains a lumen, a proximal and a distal end, wherein the guiding introducer comprises a first, second and third sections and wherein the second and third sections comprise curved portions, introducing into the lumen of said guiding introducer an ablation and mapping catheter, guiding the catheter to a selected location within the right atrium by use of the guiding introducer, and mapping and ablating the selected location in the right atrium by use of the catheter.

2. The procedure of claim 1 wherein the selected location for ablation within the right atrium comprises atrial tissue around the superior vena cava to and around the inferior vena cava.

3. The procedure of claim 1 wherein pharmacological procedures are utilized along with the ablation procedure to treat ectopic atrial tachycardia.

4. The procedure of claim 1 wherein one of the following sources of energy are utilized for ablating : direct current, radio frequency, microwave, ultrasound, laser procedures, and fulgutronization procedures.

5. The procedure of claim 4 wherein radio frequency energy is utilized.

6. The procedure of claim 1 wherein one or more non-curved guiding introducers, as well as one or more precurved, guiding introducers are utilized in conjunction with the ablation catheter to assist in the treatment of ectopic atrial tachycardia.

7. The procedure of claim 1 wherein the guiding introducer is tapered at the distal end.

8. The procedure of claim 1 wherein the guiding introducer has one or more vent holes near its distal end.

9. The procedure of claim 1 wherein the first section of the guiding introducer comprises a generally elongated, straight introducer section.

10. The procedure of claim 1 wherein the second section of the guiding introducer comprises a curved section with an inner angle from about 130° to about 180°.

11. The procedure of claim 1 wherein the third section comprises a generally straight portion and a curved portion, wherein the generally straight portion is from about 0.50 to about 2.00 in. in length, wherein the inner angle of the curved portion is curved from about 50° to about 130° and wherein the overall length of the curved portion is from about 0.20 to about 1.00 in.

12. A procedure for the treatment of ectopic atrial tachycardia within the right atrium of a human heart comprising introducing into the right atrium a precurved, guiding introducer, wherein said introducer contains a lumen, a proximal and a distal end, wherein the guiding introducer comprises a first, second and third sections and wherein the third section comprises a generally straight portion and a curved portion, introducing into the lumen of said guiding introducer an ablation and mapping catheter, guiding the catheter to a selected location within the right atrium by use of the guiding introducer, and mapping and ablating the selected location in the right atrium by use of the catheter.

13. The procedure of claim 12 Wherein the generally straight portion is from about 0.5 to about 2.00 inches in length, wherein the curved portion is curved from about 50 to about 130 degrees, and wherein the overall length of the curved portion is from about 0.20 to about 1.00 inch.

* * * * *